(12) United States Patent
Klofta et al.

(10) Patent No.: US 8,293,967 B2
(45) Date of Patent: Oct. 23, 2012

(54) DISPOSABLE ABSORBENT ARTICLES HAVING A WINDOWED SENSOR

(75) Inventors: Thomas James Klofta, Cincinnati, OH (US); Robin Lynn McKiernan, Mason, OH (US); Edward Lawrence Schmidt, Liberty Township, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 5 days.

(21) Appl. No.: 11/880,414

(22) Filed: Jul. 20, 2007

(65) Prior Publication Data
US 2008/0021429 A1    Jan. 24, 2008

Related U.S. Application Data

(60) Provisional application No. 60/832,686, filed on Jul. 21, 2006.

(51) Int. Cl.
*A61F 13/15*    (2006.01)
(52) U.S. Cl. .......................................... 604/361
(58) Field of Classification Search .................. 604/361
See application file for complete search history.

(56) References Cited

U.S. PATENT DOCUMENTS

| | | |
|---|---|---|
| 3,848,594 A | 11/1974 | Buell |
| 3,860,003 A | 1/1975 | Buell |
| 3,911,173 A | 10/1975 | Sprague, Jr. |
| 3,918,433 A * | 11/1975 | Fuisz ............................ 600/573 |
| 3,929,135 A | 12/1975 | Thompson |
| 4,121,011 A | 10/1978 | Glover et al. |
| 4,231,370 A | 11/1980 | Mroz et al. |
| 4,318,709 A | 3/1982 | Falb et al. |
| 4,324,246 A | 4/1982 | Mullane et al. |
| 4,342,314 A | 8/1982 | Radel et al. |
| 4,351,183 A | 9/1982 | Egbert |
| 4,381,781 A | 5/1983 | Sciaraffa et al. |
| 4,463,045 A | 7/1984 | Ahr et al. |
| 4,469,234 A | 9/1984 | Deussen |
| 4,515,595 A | 5/1985 | Kievit et al. |
| 4,573,986 A | 3/1986 | Minetola et al. |
| 4,607,760 A | 8/1986 | Roche |
| 4,609,518 A | 9/1986 | Curro et al. |
| 4,609,587 A | 9/1986 | Giordano et al. |

(Continued)

FOREIGN PATENT DOCUMENTS
DE        198 37 678 A1    3/2000
(Continued)

OTHER PUBLICATIONS

PTO International Search Report, mailed Feb. 26, 2008, 4 pages.
Chadha, et al., "Measurement of Urinary Concentration: A Critical Appraisal of Methodologies", Pediatric Nephrology, vol. 16, 2001, pp. 374382, SP-002244663.
A Reagent Strip for Measuring the Specific Gravity of Urine, *Clinical Chemistry*, 28/10, 2068-2072 (1982).

*Primary Examiner* — Lynne Anderson
(74) *Attorney, Agent, or Firm* — Willaim E. Gallagher; John P. Colbert

(57) ABSTRACT

A disposable absorbent article suitable for receiving and containing bodily exudates, the article comprising a front region, a back region and a crotch region disposed between said front and back region, each region having two opposing longitudinal edges, and wherein said article further comprises a window on any one of said regions for viewing a sensor suitable for measuring a condition selected from the group consisting of temperature, dehydration, rash, pH, analyte levels, humidity, and combinations thereof and wherein the sensor is placed adjacent to and facing said window placed adjacent to and facing said window.

5 Claims, 4 Drawing Sheets

U.S. PATENT DOCUMENTS

| | | |
|---|---|---|
| 4,610,678 A | 9/1986 | Weisman et al. |
| 4,629,643 A | 12/1986 | Curro et al. |
| 4,636,207 A | 1/1987 | Buell |
| 4,662,875 A | 5/1987 | Hirotsu et al. |
| 4,673,402 A | 6/1987 | Weisman et al. |
| 4,695,278 A | 9/1987 | Lawson |
| 4,699,622 A | 10/1987 | Toussant et al. |
| 4,704,115 A | 11/1987 | Buell |
| 4,705,513 A | 11/1987 | Sheldon et al. |
| 4,710,189 A | 12/1987 | Lash |
| 4,785,996 A | 11/1988 | Ziecker et al. |
| 4,795,454 A | 1/1989 | Dragoo |
| 4,808,178 A | 2/1989 | Aziz et al. |
| 4,816,025 A | 3/1989 | Foreman |
| 4,826,550 A | 5/1989 | Shimizu et al. |
| 4,834,735 A | 5/1989 | Alemany et al. |
| 4,842,666 A | 6/1989 | Werenicz |
| 4,846,815 A | 7/1989 | Scripps |
| 4,857,067 A | 8/1989 | Wood et al. |
| 4,888,231 A | 12/1989 | Angstadt |
| 4,892,536 A | 1/1990 | Desmarais et al. |
| 4,894,060 A | 1/1990 | Nestegard |
| 4,900,317 A | 2/1990 | Buell |
| 4,909,803 A | 3/1990 | Aziz et al. |
| 4,931,051 A | 6/1990 | Castello |
| 4,938,753 A | 7/1990 | Van Gompel et al. |
| 4,940,464 A | 7/1990 | Van Gompel et al. |
| 4,946,527 A | 8/1990 | Battrell |
| 4,963,140 A | 10/1990 | Robertson et al. |
| 4,968,312 A | 11/1990 | Khan |
| 4,988,344 A | 1/1991 | Reising et al. |
| 4,988,345 A | 1/1991 | Reising |
| 4,990,147 A | 2/1991 | Freeland |
| 5,006,394 A | 4/1991 | Baird |
| 5,026,364 A | 6/1991 | Robertson |
| 5,037,416 A | 8/1991 | Allen et al. |
| 5,062,840 A | 11/1991 | Holt et al. |
| 5,085,654 A | 2/1992 | Buell |
| 5,092,861 A | 3/1992 | Nomura et al. |
| 5,137,537 A | 8/1992 | Herron et al. |
| 5,140,393 A | 8/1992 | Hijikihigawa et al. |
| 5,147,345 A | 9/1992 | Young et al. |
| 5,151,092 A | 9/1992 | Buell et al. |
| 5,171,236 A | 12/1992 | Dreier et al. |
| 5,181,905 A * | 1/1993 | Flam ................ 602/41 |
| 5,197,958 A | 3/1993 | Howell |
| 5,221,228 A | 6/1993 | Pedroia |
| 5,221,274 A | 6/1993 | Buell et al. |
| 5,242,436 A | 9/1993 | Weil et al. |
| 5,246,433 A | 9/1993 | Hasse et al. |
| 5,260,345 A | 11/1993 | Desmarais et al. |
| 5,269,755 A | 12/1993 | Bodicky |
| 5,269,775 A | 12/1993 | Freeland et al. |
| 5,306,266 A | 4/1994 | Freeland |
| 5,342,338 A | 8/1994 | Roe |
| 5,387,207 A | 2/1995 | Dyer et al. |
| 5,389,093 A | 2/1995 | Howell |
| 5,397,318 A | 3/1995 | Dreier |
| RE34,920 E | 4/1995 | Aziz et al. |
| 5,458,140 A | 10/1995 | Eppstein et al. |
| 5,468,236 A | 11/1995 | Everhart et al. |
| 5,492,751 A | 2/1996 | Butt, Sr. et al. |
| 5,499,978 A | 3/1996 | Buell et al. |
| 5,507,736 A | 4/1996 | Clear et al. |
| 5,507,760 A | 4/1996 | Wynne et al. |
| 5,514,121 A | 5/1996 | Roe et al. |
| 5,518,801 A | 5/1996 | Chappell et al. |
| 5,540,671 A | 7/1996 | Dreier |
| 5,554,142 A | 9/1996 | Dreier et al. |
| 5,554,143 A | 9/1996 | Roe et al. |
| 5,554,145 A | 9/1996 | Roe et al. |
| 5,563,703 A | 10/1996 | Lebeau et al. |
| 5,569,234 A | 10/1996 | Buell et al. |
| 5,571,096 A | 11/1996 | Dobrin et al. |
| 5,580,411 A | 12/1996 | Nease et al. |
| H1630 H | 1/1997 | Roe et al. |
| 5,591,152 A | 1/1997 | Buell et al. |
| 5,607,760 A | 3/1997 | Roe |
| 5,609,587 A | 3/1997 | Roe |
| 5,625,222 A | 4/1997 | Yoneda et al. |
| 5,635,191 A | 6/1997 | Roe et al. |
| H1670 H | 7/1997 | Aziz et al. |
| 5,643,588 A | 7/1997 | Roe et al. |
| 5,653,703 A | 8/1997 | Roe et al. |
| 5,669,897 A | 9/1997 | Lavon et al. |
| 5,865,823 A | 2/1999 | Curro |
| 5,897,545 A | 4/1999 | Kline et al. |
| 5,922,283 A | 7/1999 | Hsu |
| 5,938,648 A | 8/1999 | Lavon et al. |
| 5,941,864 A | 8/1999 | Roe |
| 5,947,943 A | 9/1999 | Lee |
| 5,957,908 A | 9/1999 | Kline et al. |
| 5,968,025 A | 10/1999 | Roe et al. |
| 5,977,430 A | 11/1999 | Roe et al. |
| 5,997,520 A | 12/1999 | Ahr et al. |
| 6,004,306 A | 12/1999 | Robles et al. |
| 6,013,063 A | 1/2000 | Roe et al. |
| 6,066,774 A * | 5/2000 | Roe ................ 604/361 |
| 6,106,461 A | 8/2000 | Roskin et al. |
| 6,118,041 A | 9/2000 | Roe et al. |
| 6,120,487 A | 9/2000 | Ashton |
| 6,120,489 A | 9/2000 | Johnson et al. |
| 6,149,636 A | 11/2000 | Roe et al. |
| 6,168,584 B1 | 1/2001 | Allen et al. |
| 6,186,991 B1 | 2/2001 | Roe et al. |
| 6,200,250 B1 * | 3/2001 | Janszen ............ 493/383 |
| 6,203,496 B1 | 3/2001 | Gael et al. |
| 6,399,853 B1 | 6/2002 | Roe et al. |
| 6,432,098 B1 | 8/2002 | Kline |
| 6,476,288 B1 | 11/2002 | Vanrijswijck et al. |
| 6,479,727 B1 | 11/2002 | Roe |
| 6,501,002 B1 | 12/2002 | Roe et al. |
| 6,515,194 B2 * | 2/2003 | Neading et al. ............ 604/361 |
| 6,617,488 B1 | 9/2003 | Springer et al. |
| 6,627,787 B1 | 9/2003 | Roe et al. |
| 6,680,422 B2 | 1/2004 | Roe |
| 6,716,441 B1 | 4/2004 | Osborne et al. |
| 7,002,054 B2 | 2/2006 | Allen et al. |
| 7,105,715 B2 | 9/2006 | Carlucci et al. |
| 7,365,238 B2 * | 4/2008 | Diehl et al. ............ 604/361 |
| 2003/0014025 A1* | 1/2003 | Allen et al. ............ 604/361 |
| 2003/0158530 A1* | 8/2003 | Diehl et al. ............ 604/361 |
| 2003/0233082 A1 | 12/2003 | Kline et al. |
| 2004/0087922 A1* | 5/2004 | Bobadilla ............ 604/361 |
| 2005/0133401 A1 | 6/2005 | Lange |
| 2005/0177120 A1 | 8/2005 | Olson et al. |
| 2006/0025732 A1* | 2/2006 | Ying et al. ............ 604/361 |
| 2006/0195068 A1* | 8/2006 | Lawando ............ 604/361 |
| 2007/0270773 A1* | 11/2007 | Mackey ............ 604/361 |

FOREIGN PATENT DOCUMENTS

| | | |
|---|---|---|
| DE | 20313784 U1 | 11/2003 |
| EP | 0 114 315 B1 | 6/1987 |
| EP | 0 560 099 A2 | 9/1993 |
| EP | 0 611 966 A1 | 8/1994 |
| JP | 01-266202 A | 10/1989 |
| JP | 05-180846 A | 7/1993 |
| JP | 06-063027 A | 3/1994 |
| JP | 10-313894 A | 12/1998 |
| JP | 2001-327530 A | 11/2001 |
| JP | 2009-018183 | 1/2009 |
| WO | WO-9414395 A1 | 7/1994 |
| WO | WO-94/24557 A1 | 10/1994 |
| WO | WO-9516746 A1 | 6/1995 |
| WO | WO-9524173 A2 | 9/1995 |
| WO | WO-97/34014 A1 | 9/1997 |
| WO | WO-98/27417 A1 | 6/1998 |
| WO | WO-99/31486 A1 | 6/1999 |
| WO | WO-01/50996 A1 | 7/2001 |
| WO | WO-01/54552 A1 | 8/2001 |
| WO | WO 03/002050 A | 1/2003 |
| WO | WO 2007/077538 A | 7/2007 |

* cited by examiner

DISPOSABLE ABSORBENT ARTICLES HAVING A WINDOWED SENSOR

CROSS REFERENCE TO RELATED APPLICATION

This application claims the benefit of U.S. Provisional Application No. 60/832,686, filed Jul. 21, 2006, the substance of which is incorporated herein by reference.

FIELD OF THE INVENTION

The present invention relates to a disposable absorbent article suitable for receiving and containing bodily exudates, said article comprising a front region, a back region and a crotch region disposed between said front and back region, each region having two opposing longitudinal edges, and wherein said article further comprises a window on any one of said regions for viewing a sensor suitable for measuring a condition selected from the group consisting of temperature, dehydration, rash, pH, skin condition, analyte level, humidity, and combinations thereof and wherein the sensor is placed adjacent to and facing said window.

BACKGROUND OF THE INVENTION

One of the primary concerns of a mother of an infant is the health and wellness of the infant. As such, there are a number of diagnostic tools that have been found useful to indicate the health and wellness of infants. These tools include thermometers, analyte indicators, pH indicators, wetness indicators, etc. Oftentimes, however, these indicators are utilized primarily by professionals in clinical and health care environments rather than by caregivers. In order for these diagnostic devices to be convenient for caregivers to use, Applicants therefore thought that it would be desirable to incorporate such indicators into the daily infant care routine. One effective way of including these indicators into the routine would be integration of these indicators into the design of the disposable absorbent articles. In particular, the present invention is directed to providing a disposable absorbent article to a consumer for infant use wherein the article includes a window for facilitated viewing of a sensor. This window may be disposed on any of the outward facing surfaces of the article that allows for easy view of the sensor and the condition it is indicating.

SUMMARY OF THE INVENTION

The present invention relates to a disposable absorbent article suitable for receiving and containing bodily exudates, said article comprising a front region, a back region and a crotch region disposed between said front and back region, each region having two opposing longitudinal edges, and wherein said article further comprises a window on any one of said regions for viewing a sensor suitable for measuring a condition selected from the group consisting of temperature, dehydration, rash, pH, skin condition, analyte level, humidity, and combinations thereof and wherein the sensor is placed adjacent to and facing said window.

In another embodiment, the invention relates to a method of visually detecting an infant's health status, said method comprising the steps of:
a. providing a caregiver with a disposable absorbent article suitable for receiving and containing bodily exudates, said article comprising a front region, a back region and a crotch region disposed between said front and back region, each region having two opposing longitudinal edges, and wherein said article further comprises a window on any one of said regions for viewing a sensor suitable for measuring a condition selected from the group consisting of temperature, dehydration, rash, pH, skin condition, analyte level, humidity, and combinations thereof and wherein the sensor is placed adjacent to and facing said window and
b. donning said article onto an infant Additionally, the present invention is directed to a kit for visually detecting an infant's health status, said kit comprising:
a. one or more disposable absorbent articles suitable for receiving and containing bodily exudates, said article comprising a front region, a back region and a crotch region disposed between said front and back region, each region having two opposing longitudinal edges, and wherein said article further comprises a window on any one of said regions for viewing a sensor placed adjacent to and facing said window; and
b. one or more sensors suitable for measuring a condition selected from the group consisting of temperature, dehydration, rash, pH, skin condition, analyte level, humidity, and combinations thereof.

DETAILED DESCRIPTION OF THE INVENTION

As used herein, the term "absorbent article" refers to devices which absorb and contain body exudates and, more specifically, refers to devices which are placed against or in proximity to the body of the wearer to absorb and contain the various exudates discharged from the body. The term "disposable" is used herein to describe absorbent articles which generally are not intended to be laundered or otherwise restored or reused as absorbent articles (i.e., they are intended to be discarded after a single use and, preferably, to be recycled, composted or otherwise discarded in an environmentally compatible manner). A "unitary" absorbent article refers to absorbent articles which are formed of separate parts united together to form a coordinated entity so that they do not require separate manipulative parts like a separate holder and/or liner. A preferred embodiment of an absorbent article of the present invention is the unitary disposable absorbent article, diaper 20, shown in FIG. 1. As used herein, the terms "diaper", "training pants", "swim pants", "pull-on pants" each refers to an absorbent article generally worn by infants and incontinent persons about the lower torso. A diaper is typically fastened about the waist of an infant by a caregiver via relatively narrower tape or hook and loop tabs than training, swim, and pull-on pants which typically have relatively wider side panels that are either refastenable or non-refastenable such that the pants can be easily donned by the toddler alone. The present invention is also applicable to other absorbent articles such as incontinence briefs, incontinence undergarments, absorbent inserts, diaper holders and liners, feminine hygiene garments, wipes, bandages and the like.

Figure 1:
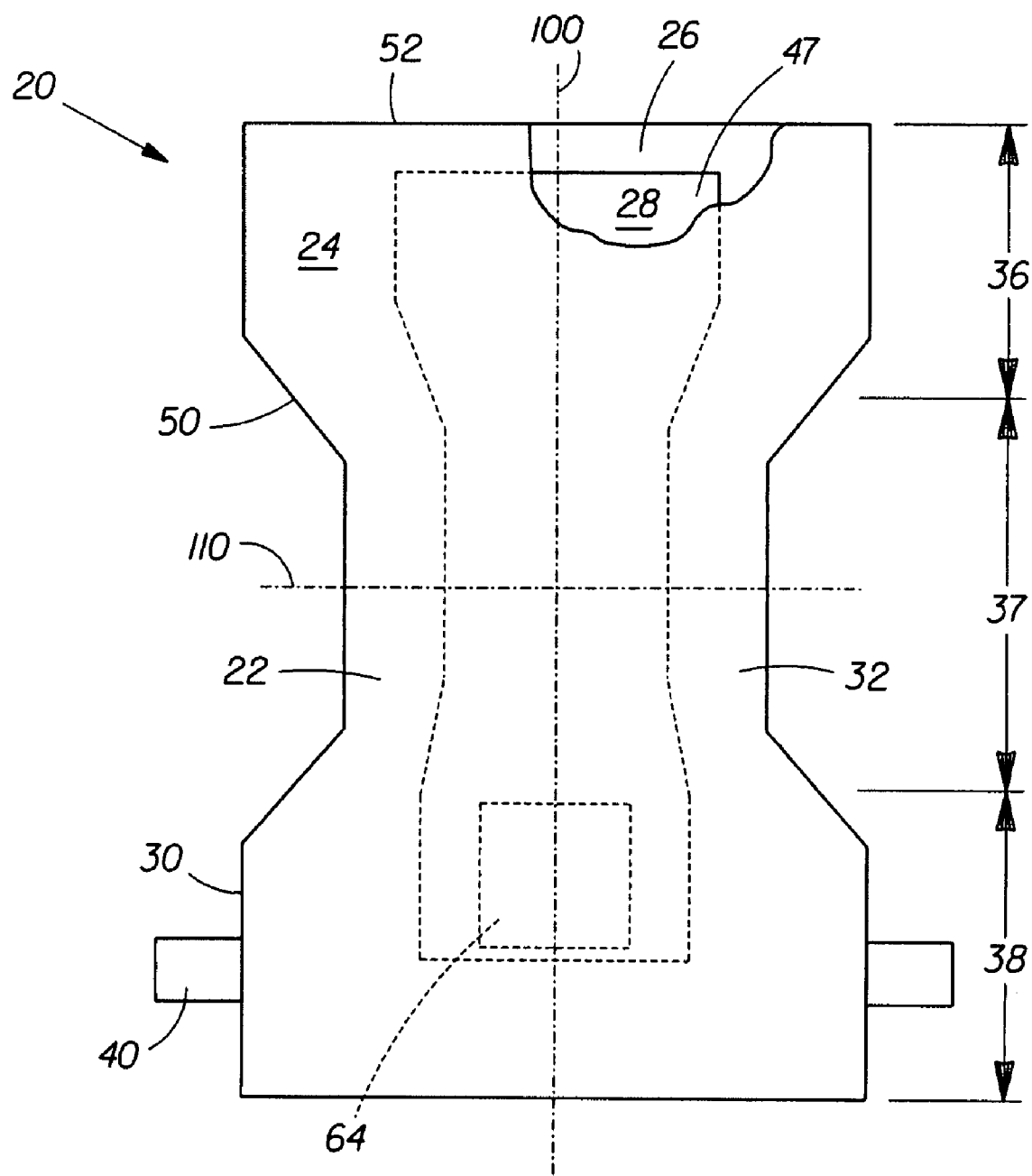
FIG. 1 is a plan view of an article made according to the present invention

FIG. 1 is a plan view of the diaper 20 of the present invention in a flat-out, state with portions of the structure being cut-away to more clearly show the construction of the diaper 20. The portion of the diaper 20 which faces the wearer is oriented towards the viewer. As shown in FIG. 1, the diaper 20 preferably comprises a liquid pervious topsheet 24; a liquid impervious backsheet 26; an absorbent core 28 which is preferably positioned between at least a portion of the topsheet 24 and the backsheet 26; side panels 30; elasticized leg cuffs 32; an elastic waist feature 34; and a fastening system generally designated 40. The diaper 20 is shown in FIG. 1 to have a first waist region 36, a second waist region 38 opposed to the first waist region 36 and a crotch region 37 located between the first waist region 36 and the second waist region 38. Each of these three regions has an exterior surface and an interior surface. The periphery of the diaper 20 is defined by the outer edges of the diaper 20 in which longitudinal edges 50 run generally parallel to the longitudinal centerline 100 of the diaper 20 and end edges 52 run between the longitudinal edges 50 generally parallel to the lateral centerline 110 of the diaper 20.

The chassis 22 of the diaper 20 comprises the main body of the diaper 20. The chassis 22 comprises at least a portion of the absorbent core 28 and preferably an outer covering including the topsheet 24 and/or the backsheet 26. If the absorbent article comprises a separate holder and a liner, the chassis 22 generally comprises the holder and the liner. (For example, the holder may comprise one or more layers of material to form the outer cover of the article and the liner may comprise an absorbent assembly including a topsheet, a backsheet, and an absorbent core. In such cases, the holder and/or the liner may include a fastening element which is used to hold the liner in place throughout the time of use.) For unitary absorbent articles, the chassis 22 comprises the main structure of the diaper with other features added to form the composite diaper structure. While the topsheet 24, the backsheet 26, and the absorbent core 28 may be assembled in a variety of well known configurations, preferred diaper configurations are described generally in U.S. Pat. No. 3,860,003 entitled "Contractible Side Portions for Disposable Diaper" issued to Kenneth B. Buell on Jan. 14, 1975; U.S. Pat. No. 5,151,092 issued to Buell on Sep. 9, 1992; and U.S. Pat. No. 5,221,274 issued to Buell on Jun. 22, 1993; and U.S. Pat. No. 5,554,145 entitled "Absorbent Article With Multiple Zone Structural Elastic-Like Film Web Extensible Waist Feature" issued to Roe et al. on Sep. 10, 1996; U.S. Pat. No. 5,569,234 entitled "Disposable Pull-On Pant" issued to Buell et al. on Oct. 29, 1996; U.S. Pat. No. 5,580,411 entitled "Zero Scrap Method For Manufacturing Side Panels For Absorbent Articles" issued to Nease et al. on Dec. 3, 1996; and U.S. Pat. No. 6,004,306 entitled "Absorbent Article With Multi-Directional Extensible Side Panels" issued to Robles et al. on Dec. 21, 1999.

The backsheet 26 is generally that portion of the diaper 20 positioned adjacent garment facing surface 45 of the absorbent core 28 which prevents the exudates absorbed and contained therein from soiling articles which may contact the diaper 20, such as bedsheets and undergarments. In preferred embodiments, the backsheet 26 is impervious to liquids (e.g., urine) and comprises a thin plastic film such as a thermoplastic film having a thickness of about 0.012 mm (0.5 mil) to about 0.051 mm (2.0 mils). Suitable backsheet films include those manufactured by Tredegar Corporation, based in Richmond, Va., and sold under the trade name CPC2 film. Other suitable backsheet materials may include breathable materials which permit vapors to escape from the diaper 20 while still preventing exudates from passing through the backsheet 26. Exemplary breathable materials may include materials such as woven webs, nonwoven webs, composite materials such as film-coated nonwoven webs, microporous films such as manufactured by Mitsui Toatsu Co., of Japan under the designation ESPOIR NO and by Tredegar Corporation of Richmond, Va. and sold under the designation EXAIRE., and monolithic films such as manufactured by Clopay Corporation, Cincinnati, Ohio under the name HYTREL blend P18-3097. Some breathable composite materials are described in greater detail in PCT Application No. WO 95/16746 published on Jun. 22, 1995 in the name of E. I. DuPont; U.S. Pat. No. 5,938,648 issued on Aug. 17, 1999 to LaVon et al.; U.S. Pat. No. 5,865,823 issued on Feb. 2, 1999 in the name of Curro; and U.S. Pat. No. 5,571,096 issued to Dobrin et al. on Nov. 5, 1996.

The backsheet 26, or any portion thereof, may be elastically extensible in one or more directions. In one embodiment, the backsheet 26 may comprise a structural elastic-like film ("SELF") web. A structural elastic-like film web is an extensible material that exhibits an elastic-like behavior in the direction of elongation without the use of added elastic materials and is described in more detail in U.S. Pat. No. 5,518,801 entitled "Web Materials Exhibiting Elastic-Like Behavior" issued to Chappell, et al. on May 21, 1996, and which is incorporated herein by reference. In alternate embodiments, the backsheet 26 may comprise elastomeric films, foams, strands, or combinations of these or other suitable materials with nonwovens or synthetic films.

The backsheet 26 may be joined to the topsheet 24, the absorbent core 28 or any other element of the diaper 20 by any attachment means known in the art. (As used herein, the term "joined" encompasses configurations whereby an element is directly secured to another element by affixing the element directly to the other element, and configurations whereby an element is indirectly secured to another element by affixing the element to intermediate member(s) which in turn are affixed to the other element.) For example, the attachment means may include a uniform continuous layer of adhesive, a patterned layer of adhesive, or an array of separate lines, spirals, or spots of adhesive. One preferred attachment means comprises an open pattern network of filaments of adhesive as disclosed in U.S. Pat. No. 4,573,986 entitled "Disposable Waste-Containment Garment", which issued to Minetola et al. on Mar. 4, 1986. Other suitable attachment means include several lines of adhesive filaments which are swirled into a spiral pattern, as is illustrated by the apparatus and methods shown in U.S. Pat. No. 3,911,173 issued to Sprague, Jr. on Oct. 7, 1975; U.S. Pat. No. 4,785,996 issued to Ziecker, et al. on Nov. 22, 1978; and U.S. Pat. No. 4,842,666 issued to Werenicz on Jun. 27, 1989. Each of these patents is incorporated herein by reference. Adhesives which have been found to be satisfactory are manufactured by H. B. Fuller Company of St. Paul, Minn. and marketed as HL-1620 and HL-1358-XZP. Alternatively, the attachment means may comprise heat bonds, pressure bonds, ultrasonic bonds, dynamic mechanical bonds, or any other suitable attachment means or combinations of these attachment means as are known in the art.

The topsheet 24 is preferably positioned adjacent body surface 47 of the absorbent core 28 and may be joined thereto and/or to the backsheet 26 by any attachment means known in the art. Suitable attachment means are described above with respect to means for joining the backsheet 26 to other elements of the diaper 20. In one preferred embodiment of the present invention, the topsheet 24 and the backsheet 26 are joined directly to each other in some locations and are indirectly joined together in other locations by directly joining them to one or more other elements of the diaper 20.

The topsheet 24 is preferably compliant, soft-feeling, and non-irritating to the wearer's skin. Further, at least a portion of the topsheet 24 is liquid pervious, permitting liquids to readily penetrate through its thickness. A suitable topsheet may be manufactured from a wide range of materials, such as porous foams, reticulated foams, apertured plastic films, or woven or nonwoven materials of natural fibers (e.g., wood or cotton fibers), synthetic fibers (e.g., polyester or polypropylene fibers), or a combination of natural and synthetic fibers. If the topsheet 24 includes fibers, the fibers may be spunbond, carded, wet-laid, meltblown, hydroentangled, or otherwise processed as is known in the art. One suitable topsheet 24 comprising a web of staple-length polypropylene fibers is manufactured by Veratec, Inc., a Division of International Paper Company, of Walpole, Mass. under the designation P-8.

Suitable formed film topsheets are described in U.S. Pat. No. 3,929,135, entitled "Absorptive Structures Having Tapered Capillaries" issued to Thompson on Dec. 30, 1975; U.S. Pat. No. 4,324,246 entitled "Disposable Absorbent Article Having A Stain Resistant Topsheet" issued to Mullane, et al. on Apr. 13, 1982; U.S. Pat. No. 4,342,314 entitled "Resilient Plastic Web Exhibiting Fiber-Like Properties" issued to Radel, et al. on Aug. 3, 1982; U.S. Pat. No. 4,463,045 entitled "Macroscopically Expanded Three-Dimensional Plastic Web Exhibiting Non-Glossy Visible Surface and Cloth-Like Tactile Impression" issued to Ahr, et al. on Jul. 31, 1984; and U.S. Pat. No. 5,006,394 "Multilayer Polymeric Film" issued to Baird on Apr. 9, 1991. Other suitable topsheets 30 may be made in accordance with U.S. Pat. Nos. 4,609,518 and 4,629,643 issued to Curro et al. on Sep. 2, 1986 and Dec. 16, 1986, respectively, and both of which are incorporated herein by reference. Such formed films are available from The Procter & Gamble Company of Cincinnati, Ohio as "DRI-WEAVE" and from Tredegar Corporation, based in Richmond, Va., as "CLIFF-T."

Preferably, at least a portion of the topsheet 24 is made of a hydrophobic material or is treated to be hydrophobic in order to isolate the wearer's skin from liquids contained in the absorbent core 28. If the topsheet 24 is made of a hydrophobic material, preferably at least a portion of the upper surface of the topsheet 24 is treated to be hydrophilic so that liquids will transfer through the topsheet more rapidly. The topsheet 24 can be rendered hydrophilic by treating it with a surfactant or by incorporating a surfactant into the topsheet. Suitable methods for treating the topsheet 24 with a surfactant include spraying the topsheet 24 material with the surfactant and/or immersing the material into the surfactant. A more detailed discussion of such a treatment and hydrophilicity is contained in U.S. Pat. No. 4,988,344 entitled "Absorbent Articles with Multiple Layer Absorbent Layers" issued to Reising, et al. on Jan. 29, 1991 and U.S. Pat. No. 4,988,345 entitled "Absorbent Articles with Rapid Acquiring Absorbent Cores" issued to Reising on Jan. 29, 1991. A more detailed discussion of some suitable methods for incorporating a surfactant in the topsheet 24 can be found in U.S. Statutory Invention Registration No. H1670 published on Jul. 1, 1997 in the names of Aziz et al. Each of these references is hereby incorporated by reference herein. Alternatively, the topsheet 24 may include an apertured web or film which is hydrophobic. This may be accomplished by eliminating the hydrophilizing treatment step from the production process and/or applying a hydrophobic treatment to the topsheet 24, such as a polytetraflouroethylene compound like SCOTCHGUARD or a hydrophobic lotion composition, as described below. In such embodiments, it is preferred that the apertures be large enough to allow the penetration of aqueous fluids like urine without significant resistance.

Any portion of the topsheet 24 may be coated with a lotion as is known in the art. Examples of suitable lotions include those described in U.S. Pat. No. 5,607,760 entitled "Disposable Absorbent Article Having A Lotioned Topsheet Containing an Emollient and a Polyol Polyester Immobilizing Agent" issued to Roe on Mar. 4, 1997; U.S. Pat. No. 5,609,587 entitled "Diaper Having A Lotion Topsheet Comprising A Liquid Polyol Polyester Emollient And An Immobilizing Agent" issued to Roe on Mar. 11, 1997; U.S. Pat. No. 5,635,191 entitled "Diaper Having A Lotioned Topsheet Containing A Polysiloxane Emollient" issued to Roe et al. on Jun. 3, 1997; U.S. Pat. No. 5,643,588 entitled "Diaper Having A Lotioned Topsheet" issued to Roe et al. on Jul. 1, 1997; U.S. Pat. No. 5,968,025 entitled "Absorbent Article Having a Lotioned Topsheet" issued to Roe et al. on Oct. 19, 1999 and U.S. Pat. No. 6,716,441 entitled "Compositions for the efficient release of active ingredients" issued to Osborne on Apr. 6, 2004. The lotion may function alone or in combination with another agent as the hydrophobizing treatment described above. The topsheet 24 may also include or be treated with antibacterial agents, some examples of which are disclosed in PCT Publication No. WO 95/24173 entitled "Absorbent Articles Containing Antibacterial Agents in the Topsheet For Odor Control" which was published on Sep. 14, 1995 in the name of Theresa Johnson. Further, the topsheet 24, the backsheet 26 or any portion of the topsheet or backsheet may be embossed and/or matte finished to provide a more cloth like appearance.

The topsheet 24 may comprise one or more apertures to ease penetration of exudates therethrough, such as urine and/or feces (solid, semi-solid, or liquid). The size of at least the primary aperture is important in achieving the desired waste encapsulation performance. If the primary aperture is too small, the waste may not pass through the aperture, either due to poor alignment of the waste source and the aperture location or due to fecal masses having a diameter greater than the aperture. If the aperture is too large, the area of skin that may be contaminated by "rewet" from the article is increased. Typically, the aperture should have an area of between about 10 $cm^2$ and about 50 $cm^2$. The aperture preferably has an area of between about 15 $cm^2$ and 35 $cm^2$.

Further, the topsheet 24 may be fully or partially elasticated or may be foreshortened so as to provide a void space between the topsheet 24 and the core 28. Exemplary structures including elasticized or foreshortened topsheets are described in more detail in U.S. Pat. No. 4,892,536 issued to DesMarais et al. on Jan. 9, 1990 entitled "Absorbent Article Having Elastic Strands"; U.S. Pat. No. 4,990,147 issued to Freeland on Feb. 5, 1991 entitled "Absorbent Article With Elastic Liner For Waste Material Isolation"; U.S. Pat. No. 5,037,416 issued to Allen et al. on Aug. 6, 1991 entitled "Disposable Absorbent Article Having Elastically Extensible Topsheet"; and U.S. Pat. No. 5,269,775 issued to Freeland et al. on Dec. 14, 1993 entitled "Trisection Topsheets For Disposable Absorbent Articles and Disposable Absorbent Articles Having Such Trisection Topsheets"; each of which is incorporated by reference herein.

The absorbent core 28 may comprise any absorbent material which is generally compressible, conformable, non-irritating to the wearer's skin, and capable of absorbing and retaining liquids such as urine and other certain body exudates. The absorbent core 28 may be manufactured in a wide variety of sizes and shapes (e.g., rectangular, hourglass, "T"-shaped, asymmetric, etc.) and may comprise a wide variety of liquid-absorbent materials commonly used in disposable diapers and other absorbent articles such as comminuted wood pulp, which is generally referred to as airfelt. Examples of other suitable absorbent materials include creped cellulose wadding; meltblown polymers, including coform; chemically stiffened, modified or cross-linked cellulosic fibers; tissue, including tissue wraps and tissue laminates; absorbent foams; absorbent sponges; superabsorbent polymers; absorbent gelling materials; or any other known absorbent material or combinations of materials.

The configuration and construction of the absorbent core 28 may also be varied (e.g., the absorbent core(s) or other absorbent structure(s) may have varying caliper zones, hydrophilic gradient(s), a superabsorbent gradient(s), or lower average density and lower average basis weight acquisition zones; or may comprise one or more layers or structures). Exemplary absorbent structures for use as the absorbent core 28 are described in U.S. Pat. No. 4,610,678 entitled "High-Density Absorbent Structures" issued to Weisman et al. on Sep. 9, 1986; U.S. Pat. No. 4,673,402 entitled "Absorbent Articles With Dual-Layered Cores" issued to Weisman et al. on Jun. 16, 1987; U.S. Pat. No. 4,834,735 entitled "High Density Absorbent Members Having Lower Density and Lower Basis Weight Acquisition Zones" issued to Alemany et al. on May 30, 1989; U.S. Pat. No. 4,888,231 entitled "Absorbent Core Having A Dusting Layer" issued to Angstadt on Dec. 19, 1989; U.S. Pat. No. 5,137,537 entitled "Absorbent Structure Containing Individualized, Polycarboxylic Acid Crosslinked Wood Pulp Cellulose Fibers" issued to Herron et al. on Aug. 11, 1992; U.S. Pat. No. 5,147,345 entitled "High Efficiency Absorbent Articles For Incontinence Management" issued to Young et al. on Sep. 15, 1992; U.S. Pat. No. 5,342,338 entitled "Disposable Absorbent Article For Low-Viscosity Fecal Material" issued to Roe on Aug. 30, 1994; U.S. Pat. No. 5,260,345 entitled "Absorbent Foam Materials For Aqueous Body Fluids and Absorbent Articles Containing Such Materials" issued to DesMarais et al. on Nov. 9, 1993; U.S. Pat. No. 5,387,207 entitled "Thin-Until-Wet Absorbent Foam Materials For Aqueous Body Fluids And Process For Making Same" issued to Dyer et al. on Feb. 7, 1995; and U.S. Pat. No. 5,625,222 entitled "Absorbent Foam Materials For Aqueous Fluids Made From High Internal Phase Emulsions Having Very High Water-To-Oil Ratios" issued to DesMarais et al. on Jul. 22, 1997. Each of these patents is incorporated herein by reference.

The diaper 20 may also include a sublayer disposed between the topsheet 24 and the backsheet 26. (As used herein, the term "disposed" is used to mean that an element(s) of the diaper is formed (joined and positioned) in a particular place or position as a unitary structure with other elements of the diaper or as a separate element joined to another element of the diaper.) The sublayer may be any material or structure capable of accepting, storing or immobilizing bodily exudates. Thus, the sublayer may include a single material or a number of materials operatively associated with each other. Further, the sublayer may be integral with another element of the diaper 20 or may be one or more separate elements joined directly or indirectly with one or more elements of the diaper 20. Further, the sublayer may include a structure that is separate from the core 28 or may include or be part of at least a portion of the core 28.

Suitable materials for use as the sublayer may include large cell open foams, macro-porous compression resistant nonwoven highlofts, large size particulate forms of open and closed cell foams (macro and/or microporous), highloft nonwovens, polyolefin, polystyrene, polyurethane foams or particles, structures comprising a multiplicity of vertically oriented looped strands of fibers, absorbent core structures described above having punched holes or depressions, and the like. (As used herein, the term "microporous" refers to materials which are capable of transporting fluids by capillary action. The term "macroporous" refers to materials having pores too large to effect capillary transport of fluid, generally having pores greater than about 0.5 mm in diameter and, more specifically, having pores greater than about 1.0 mm in diameter.) One embodiment of a sublayer includes a mechanical fastening loop landing element, having an uncompressed thickness of about 1.5 millimeters available as XPL-7124 from the 3M Corporation of Minneapolis, Minn. Another embodiment includes a 6 denier, crimped and resin-bonded nonwoven highloft having a basis weight of 110 grams per square meter and an uncompressed thickness of 7.9 millimeters which is available from the Glit Company of Wrens, Ga. Other suitable absorbent and nonabsorbent sublayers are described in U.S. Pat. No. 6,680,422 entitled "Disposable Absorbent Article Having Capacity to Store Low-Viscosity Fecal Material" issued to Roe on Jan. 20, 2004 and U.S. Pat. No. 5,941,864 entitled "Disposable Absorbent Article Having Improved Fecal Storage" issued to Roe on Aug. 24, 1999, both of which are hereby incorporated by reference herein. Further, the sublayer, or any portion thereof, may include or be coated with a lotion or other known substances to add, enhance or change the performance or other characteristics of the element.

The diaper 20 may also comprise at least one elastic waist feature 34 that helps to provide improved fit and containment. The elastic waist feature 34 is generally intended to elastically expand and contract to dynamically fit the wearer's waist. The elastic waist feature 34 preferably extends at least longitudinally outwardly from at least one waist edge of the absorbent core 28 and generally forms at least a portion of the end edge 52 of the diaper 20. Disposable diapers are often constructed so as to have two elastic waist features, one positioned in the first waist region 36 and one positioned in the second waist region 38. Further, while the elastic waist feature 34 or any of its constituent elements may comprise one or more separate elements affixed to the diaper 20, the elastic waist feature 34 may be constructed as an extension of other elements of the diaper 20, such as the backsheet 26, the topsheet 24, or both the backsheet 26 and the topsheet 24.

The elastic waist feature 34 may be constructed in a number of different configurations including those described in U.S. Pat. No. 4,515,595 issued to Kievit et al. on May 7, 1985; U.S. Pat. No. 4,710,189 issued to Lash on Dec. 1, 1987; U.S. Pat. No. 5,151,092 issued to Buell on Sep. 9, 1992; and U.S. Pat. No. 5,221,274 issued to Buell on Jun. 22, 1993. Other suitable waist configurations may include waistcap features such as those described in U.S. Pat. No. 5,026,364 issued to Robertson on Jun. 25, 1991 and U.S. Pat. No. 4,816,025 issued to Foreman on Mar. 28, 1989.

The diaper 20 may also include a fastening system 40. The fastening system 40 preferably maintains the first waist region 36 and the second waist region 38 in a configuration so as to provide lateral tensions about the circumference of the diaper 20 to hold the diaper 20 on the wearer. The fastening system 40 preferably comprises a fastener such as tape tabs, hook and loop fastening components, interlocking fasteners such as tabs & slots, buckles, buttons, snaps, and/or hermaphroditic fastening components, although any other known fastening means are generally acceptable. Some exemplary surface fastening systems are disclosed in U.S. Pat. No. 3,848,594 entitled "Tape Fastening System for Disposable Diaper" issued to Buell on Nov. 19, 1974; U.S. Pat. No. B1 4,662,875 entitled "Absorbent Article" issued to Hirotsu et al. on May 5, 1987; U.S. Pat. No. 4,846,815 entitled "Disposable Diaper Having An Improved Fastening Device" issued to Scripps on Jul. 11, 1989; U.S. Pat. No. 4,894,060 entitled "Disposable Diaper With Improved Hook Fastener Portion" issued to Nestegard on Jan. 16, 1990; U.S. Pat. No. 4,946,527 entitled "Pressure-Sensitive Adhesive Fastener And Method of Making Same" issued to Battrell on Aug. 7, 1990; the herein before referenced U.S. Pat. No. 5,151,092 issued to Buell on Sep. 9, 1992; and U.S. Pat. No. 5,221,274 issued to Buell on Jun. 22, 1993. An exemplary interlocking fastening system is disclosed in co-pending U.S. Pat. No. 6,432,098 entitled "Absorbent Article Fastening Device" in the names of Kline et al. issued on Aug. 13, 2002. The fastening system 40 may also provide a means for holding the article in a disposal configuration as disclosed in U.S. Pat. No. 4,963,140 issued to Robertson et al. on Oct. 16, 1990. The fastening system may also include primary and secondary fastening systems, as disclosed in U.S. Pat. No. 4,699,622 entitled "Disposable Diaper Having An Improved Side Closure" issued to Toussant et al. on Oct. 13, 1987. to reduce shifting of overlapped portions or to improve fit as disclosed in U.S. Pat. No. 5,242,436 entitled "Absorbent Article With Fastening System Providing Dynamic Elasticized Waistband Fit" issued to Weil et al. on Sep. 7, 1993; U.S. Pat. No. 5,499,978 entitled "Absorbent Article With Dynamic Elastic Waist Feature Having A Predisposed Resilient Flexural Hinge" issued to Buell et al. on Mar. 19, 1996; U.S. Pat. No. 5,507,736 entitled "Absorbent Article With Dynamic Elastic Waist Feature Comprising An Expansive Tummy Panel" issued to Clear et al. on Apr. 16, 1996; U.S. Pat. No. 5,591,152 entitled "Absorbent Article With Dynamic Elastic Waist Feature Having A Predisposed Resilient Flexural Hinge" issued to Buell et al. on Jan. 7, 1997.

Figure 4:
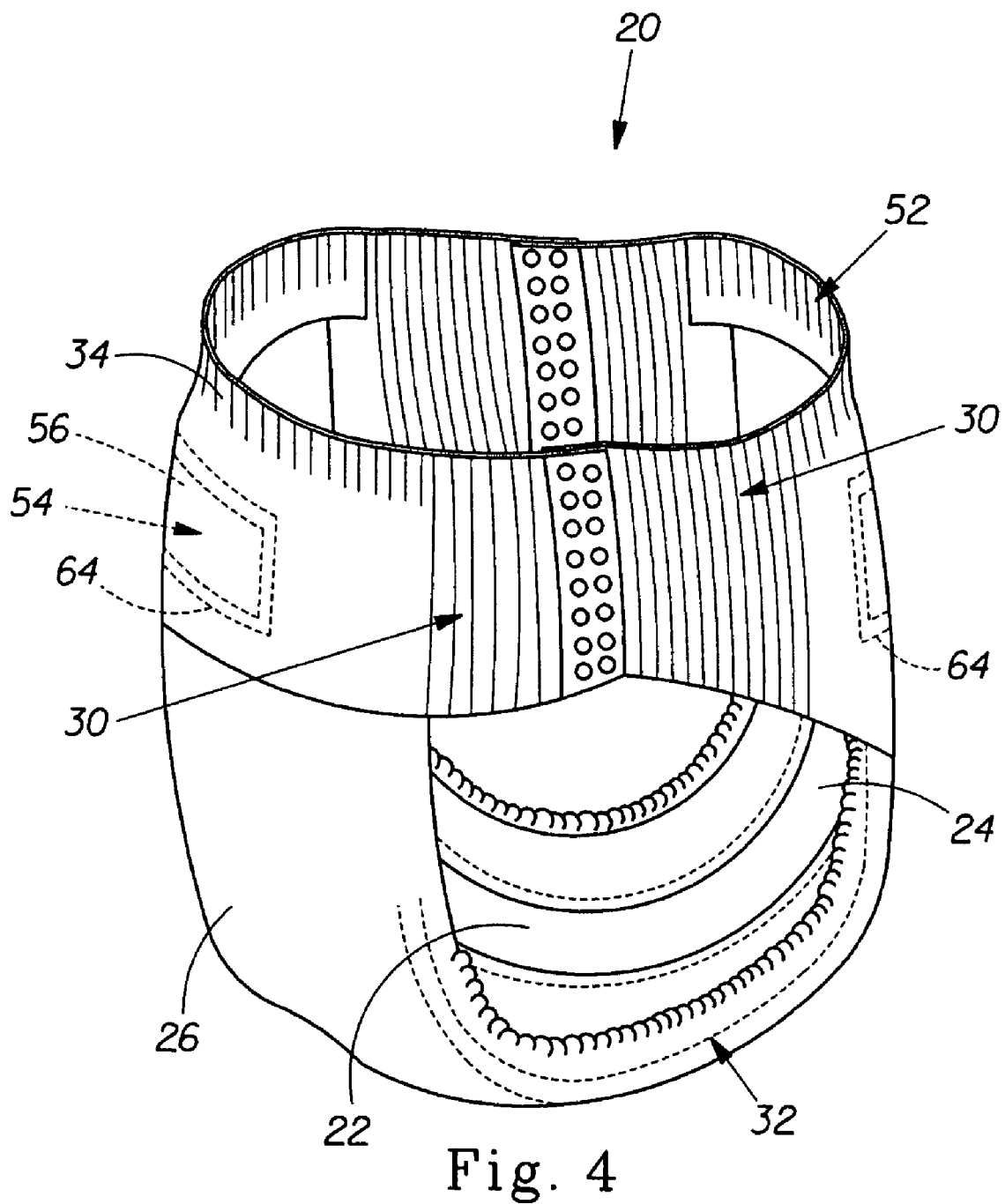
FIG. 4 is a perspective view of a disposable pant-type garment made according to the present invention.

In certain embodiments, the article may be preformed by the manufacturer to create a pant-type diaper as shown in FIG. 4. The terms "pant" or "pant-type diaper", as used herein, refers to disposable garments having a waist opening and leg openings designed for infant or adult wearers. A pant may be placed in position on the wearer by inserting the wearer's legs into the leg openings and sliding the pant into position about the wearer's lower torso. A pant may be preformed by any suitable technique including, but not limited to, joining together portions of the article using refastenable and/or non-refastenable bonds (e.g., seam, weld, adhesive, cohesive bond, fastener, etc.). A pant may be preformed anywhere along the circumference of the article (e.g., side fastened, front waist fastened). While the term "pant" is used herein, pants are also commonly referred to as "closed diapers", "prefastened diapers", "pull-on diapers", "training pants" and "diaper-pants". Suitable pants are disclosed in U.S. Pat. No. 5,246,433, issued to Hasse, et al. on Sep. 21, 1993; U.S. Pat. No. 5,569,234, issued to Buell et al. on Oct. 29, 1996; U.S. Pat. No. 6,120,487, issued to Ashton on Sep. 19, 2000; U.S. Pat. No. 6,120,489, issued to Johnson et al. on Sep. 19, 2000; U.S. Pat. No. 4,940,464, issued to Van Gompel et al. on Jul. 10, 1990; U.S. Pat. No. 5,092,861, issued to Nomura et al. on Mar. 3, 1992; U.S. patent application Ser. No. 10/171,249, entitled "Highly Flexible And Low Deformation Fastening Device", filed on Jun. 13, 2002; U.S. Pat. No. 5,897,545, issued to Kline et al. on Apr. 27, 1999; U.S. Pat. No. 5,957,908, issued to Kline et al on Sep. 28, 1999.

The diaper 20 may also comprise side panels 30. The side panels 30 may be elastic or extensible to provide a more comfortable and contouring fit by initially conformably fitting the diaper 20 to the wearer and sustaining this fit throughout the time of wear well past when the diaper 20 has been loaded with exudates since the elasticized side panels 30 allow the sides of the diaper 20 to expand and contract. The side panels 30 may also provide more effective application of the diaper 20 because even if the diaperer pulls one elasticized side panel 30 farther than the other during application, the diaper 20 will "self-adjust" during wear.

While the diaper 20 of the present invention preferably has the side panels 30 disposed in the second waist region 38, the diaper 20 may be provided with side panels 30 disposed in the first waist region 36 or in both the first waist region 36 and the second waist region 38. The side panels 30 may be constructed in any suitable configurations. Examples of diapers with elasticized side panels are disclosed in U.S. Pat. No. 4,857,067, entitled "Disposable Diaper Having Shirred Ears" issued to Wood, et al. on Aug. 15, 1989; U.S. Pat. No. 4,381,781 issued to Sciaraffa, et al. on May 3, 1983; U.S. Pat. No. 4,938,753 issued to Van Gompel, et al. on Jul. 3, 1990; the herein before referenced U.S. Pat. No. 5,151,092 issued to Buell on Sep. 9, 1992; U.S. Pat. No. 5,221,274 issued to Buell on Jun. 22, 1993; U.S. Pat. No. 5,669,897 issued to LaVon, et al. on Sep. 23, 1997 entitled "Absorbent Articles Providing Sustained Dynamic Fit"; and U.S. Pat. No. 6,004,306 entitled "Absorbent Article With Multi-Directional Extensible Side Panels" issued to Robles et al. on Dec. 21, 1999

The diaper 20 preferably further includes leg cuffs 32 which provide improved containment of liquids and other body exudates. Leg cuffs 32 may also be referred to as leg bands, side flaps, barrier cuffs, or elastic cuffs. U.S. Pat. No. 3,860,003 describes a disposable diaper which provides a contractible leg opening having a side flap and one or more elastic members to provide an elasticized leg cuff (a gasketing cuff). U.S. Pat. Nos. 4,808,178 and 4,909,803 issued to Aziz et al. on Feb. 28, 1989 and Mar. 20, 1990, respectively, describe disposable diapers having "stand-up" elasticized flaps (barrier cuffs) which improve the containment of the leg regions. U.S. Pat. Nos. 4,695,278 and 4,795,454 issued to Lawson on Sep. 22, 1987 and to Dragoo on Jan. 3, 1989, respectively, describe disposable diapers having dual cuffs, including gasketing cuffs and barrier cuffs. In some embodiments, it may be desirable to treat all or a portion of the leg cuffs 32 with a lotion, as described above.

Embodiments of the present invention may also include pockets for receiving and containing waste, spacers which provide voids for waste, barriers for limiting the movement of waste in the article, compartments or voids which accept and contain waste materials deposited in the diaper 20, and the like, or any combinations thereof. Examples of pockets and spacers for use in absorbent products are described in U.S. Pat. No. 5,514,121 issued to Roe et al. on May 7, 1996, entitled "Diaper Having Expulsive Spacer"; U.S. Pat. No. 5,171,236 issued to Dreier et al. on Dec. 15, 1992 entitled "Disposable Absorbent Article Having Core Spacers"; U.S. Pat. No. 5,397,318 issued to Dreier on Mar. 14, 1995 entitled "Absorbent Article Having A Pocket Cuff"; U.S. Pat. No. 5,540,671 issued to Dreier on Jul. 30, 1996 entitled "Absorbent Article Having A Pocket Cuff With An Apex"; U.S. Pat. No. 6,168,584 entitled "Spacers For Use In Hygienic Absorbent Articles And Disposable Absorbent Articles Having Such Spacer" issued to Allen et al. on Jan. 2, 2001; U.S. Pat. No. 5,306,266 entitled "Flexible Spacers For Use In Disposable Absorbent Articles" issued to Freeland on Apr. 26, 1994; and U.S. Pat. No. 5,997,520 entitled "Disposable Absorbent Article With Selectively Expandable or Inflatable Component" issued to Ahr et al. on Dec. 7, 1999. Examples of compartments or voids are disclosed in U.S. Pat. No. 4,968,312 entitled "Disposable Fecal Compartmenting Diaper" issued to Khan on Nov. 6, 1990; U.S. Pat. No. 4,990,147 entitled "Absorbent Article With Elastic Liner For Waste Material Isolation" issued to Freeland on Feb. 5, 1991; U.S. Pat. No. 5,062,840, entitled "Disposable Diapers" issued to Holt et al on Nov. 5, 1991; and U.S. Pat. No. 5,269,755 entitled "Trisection Topsheets For Disposable Absorbent Articles And Disposable Absorbent Articles Having Such Trisection Topsheets" issued to Freeland et al on Dec. 14, 1993. Examples of suitable transverse barriers are described in U.S. Pat. No. 5,554,142 entitled "Absorbent Article Having Multiple Effective Height Transverse Partition" issued Sep. 10, 1996 in the name of Dreier et al.; PCT Patent WO 94/14395 entitled "Absorbent Article Having An Upstanding Transverse Partition" published Jul. 7, 1994 in the name of Freeland, et al.; and U.S. Pat. No. 5,653,703 Absorbent Article Having Angular Upstanding Transverse Partition issued Aug. 5, 1997 to Roe, et al. Examples of other structures especially suitable for management of low viscosity feces are disclosed in U.S. Pat. No. 5,941,864 issued to Roe et al. on Aug. 24, 1999; U.S. Pat. No. 5,977,430 issued to Roe et al. on Nov. 2, 1999 and U.S. Pat. No. 6,013,063 issued to Roe et al. on Jan. 11, 2000.

Figure 2:
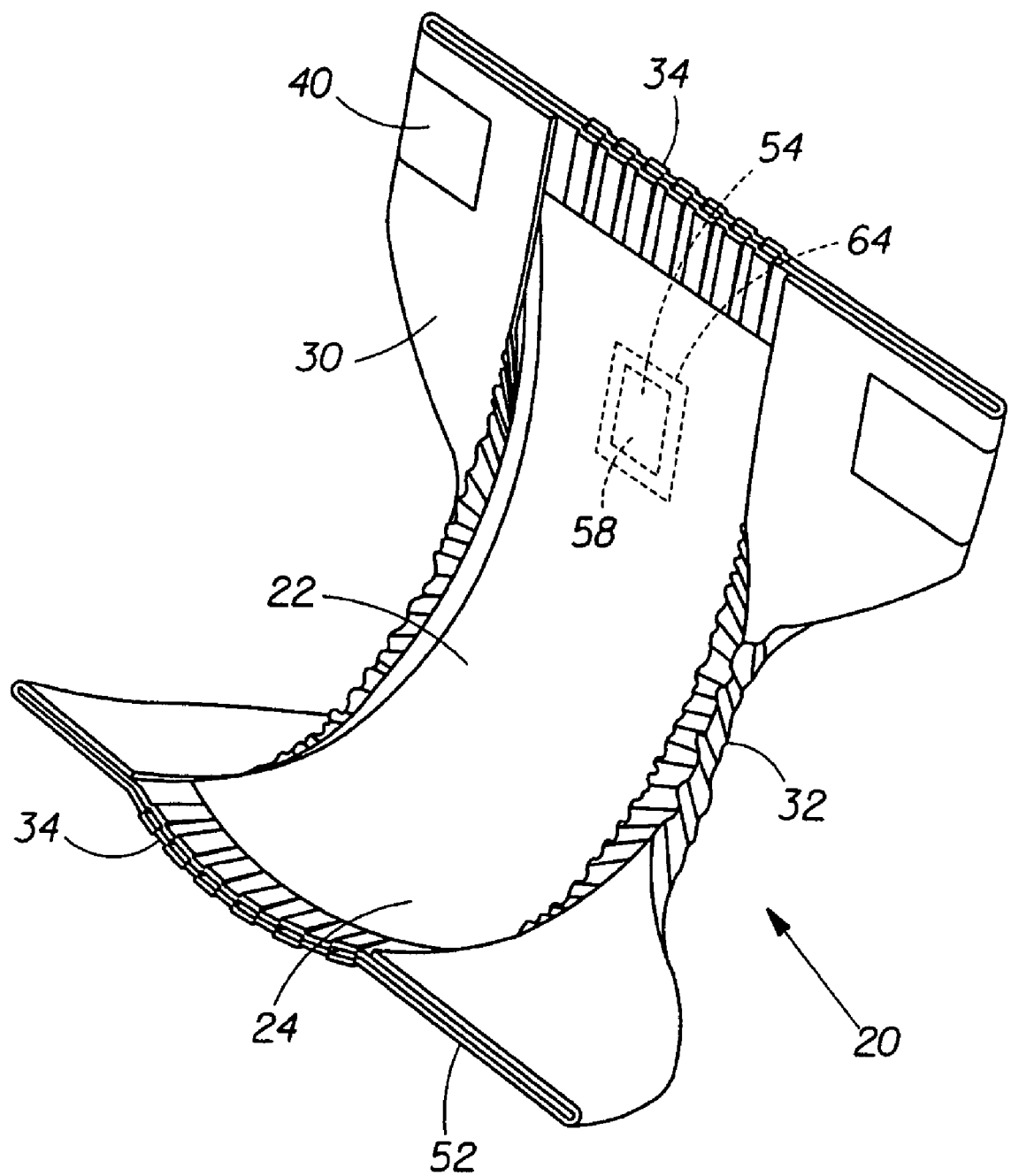
FIG. 2 is a top perspective view of the diaper of FIG. 1.
Figure 3:
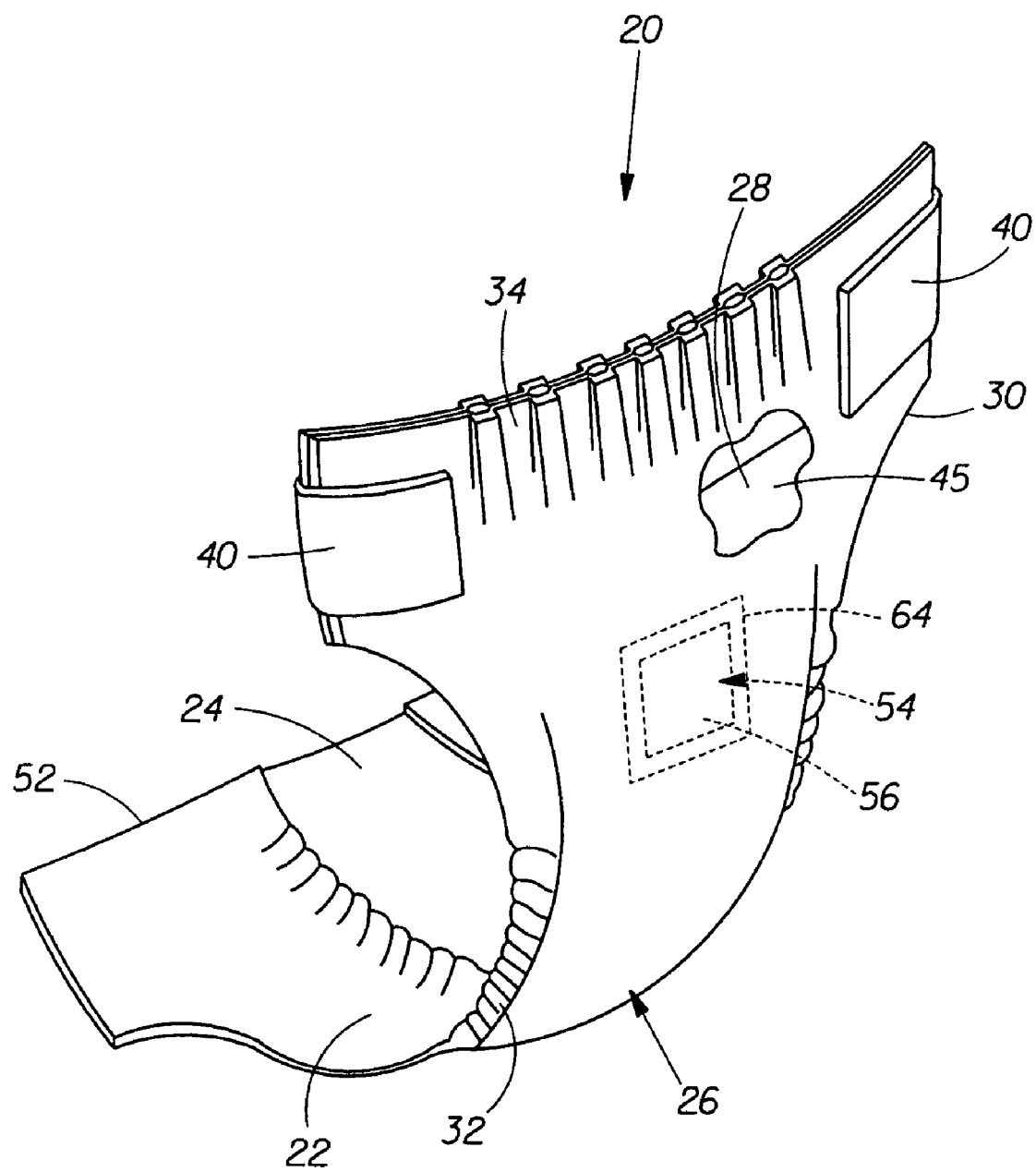
FIG. 3 is a back perspective view of the diaper of FIG. 1.

As shown in FIGS. 1-3 in diaper 20 of the present invention, a window 64 is provided to enable an indication of the condition of the wearer of the article through which a sensor is easily viewable from the outside of the diaper. The window 64 may be disposed on an exterior surface of any one of the first waist, second waist, or crotch regions. In certain embodiments, a window 64 is disposed on the first and second waist regions. This indication is made apparent by the insertion of a sensor 54 that is useful for determining changes conditions that are pertinent to an infant's wellbeing including, but not necessarily limited to, body temperature, environmental temperature, pH, skin condition, analyte levels, etc. The window has two opposing surfaces, i.e., an external facing surface 56 and an internal facing surface 58.

The sensor of the present invention may comprise one or more thermochromic materials selected from the group consisting of thermochromic liquid crystalline materials, thermochromic inks, thermochromic dyes, and combinations thereof. The materials are intended to serve as temperature indication mechanisms within the sensor. As used herein "thermochromic" means materials/inks/dyes that change color as a function of temperature. In particular, thermochromic dyes that can change color are called leuco dyes and such can be directly mixed in films, nonwovens, and elastics and are commercially available from HW Sands Corp in Jupiter Fla. and Color Change Corp in Streamwood Ill. In any instance, however, suitable thermochromic liquid crystalline materials may be either temperature sensitive or temperature insensitive and chiral or cholesteric in nature. The thermochromic inks are commercially available from Chromatic Technologies, Inc. under the tradename Dynacolor® as body temperature or high temperature inks or from Sun Chemical's AIC subsidiary of France under the name ThermaSOFT®. Additional suitable thermochromic inks are detailed in U.S. Pat. Nos. 4,121,011, 4,826,550, 5,389,093, and 5,221,228. The thermochromic materials used can be in the form of fine pigments particles, microencapsulated materials, molecular materials and the like.

The one or more materials may be is applied in an application method selected from the group consisting of spraying, printing, coating, painting, and combinations thereof. Suitable printing methods include, but are not limited to gravure, flexo, inkjet, slot, and screen printing.

In certain instances, the temperature insensitive (or shear sensitive or clearing point) thermochromic liquid crystalline material is colored at room temperature and normal human body temperatures and changes to clear in appearance in response to a noticeable increase in human body temperature. However, there are other suitable types of thermochromic liquid crystalline materials (temperature sensitive) that turn from colorless to red to orange to yellow to green to blue to violet and then back to colorless as the temperature is increased. Suitable materials for use in the sensor of the present invention materials include chiral and/or cholesteric thermochromic liquid crystalline materials like those incorporated into patches sold by Hallcrest Incorporated (Glenview, Ill.), Kaz Inc. (Hudson, N.Y.), Liquid Crystal Resources, LLC (Glenview, Ill.), Medical Indicators (Pennington, N.Y.), Thermographic Measurements (Flintshire, UK), all of which both make thermochromic liquid crystalline based patches for application to the skin in order to measure the core body temperature. Also, the thermochromic liquid crystalline material may be incorporated into a multi-layered sensor beneath which is disposed an underlayment layer 58. In most instances, this layer comprises a polymeric material selected from the group consisting of polyolefin, polyester, polyvinyl chloride, or a combination thereof. In particular, the polyolefin material may be selected from the group consisting of polyethylene, polypropylene, and combinations thereof. This underlayment layer is typically printed black to enhance the appearance of the thermochromic liquid crystalline material phase transformations but this underlayment layer may also may be printed to be colored such that this underlayment layer becomes visible in the sensor through the thermochromic liquid crystalline material as it becomes transparent or translucent in appearance. Alternatively, the underlayment layer may also comprise photochromic ink. Photochromic inks change color in response to the presence of ultraviolet or other wavelengths of radiation. In most cases, the photochromic inks change from invisible or clear to a humanly perceivable color upon exposure to a particular range of wavelengths. Additionally, an overlayment layer may be used on an opposing surface of the sensor from the underlayment layer to aid in the containment of the thermochromic material. This contributes to the removability of the sensor from the window for even easier viewing. The overlayment layer may be made from the same materials as the underlayment layer. Further detail of a sensor that is suitable for incorporation into the present invention is described in U.S. provisional application Ser. No. 60/756,237 filed on Jan. 3, 2006 in the names of Klofta et al.

Alternatively, urinalysis test strips may be used since they give a quick reading of various constituents in urine. The Combur-Test™ urinalysis test strips marketed by Roche (Geneva) can test for leukocytes, pH, bilirubin, blood, specific gravity, and other analytes in urine. These test strips have been found useful for the early diagnosis of kidney and liver diseases, as well as in the early detection of diabetes, urinary tract infections, and even dehydration. An exemplary pH indicator is a laboratory pH test strip made by Roche Chemicals (Abilene, Tex.). Suitable humidity measuring indicators may be commercially available from Omega in Connecticut. Another test strip that may be used as a non-electronic sensor in the context of the present invention is a feces analysis test strip. For instance, W.H.P.M. Incorporated (El Monte, Calif.) manufactures an immunoassay based test strip for the detection of hemoglobin. This test is based on dye conjugate immunoassays using combinations of monoclonal and polyclonal antibodies to detect hemoglobin and is useful in the early recognition of colorectal cancer or other gastrointestinal disorders. Although such ailments are not common in infants, they can be common in elderly wearers of adult incontinence products that are encompassed within the present invention.

In certain embodiments, the sensor may be attached to the window via an attachment mechanism like an adhesive or a hook and loop fastener on at least one surface to ensure prolonged placement and stability within the window once applied. Both the window 64 and the sensor 54 may take a variety of shapes within the article and both elements need not necessarily be the same shape. For instance, the elements can be circular, square, elliptical, triangular, rectangular, or in the form of a graphic of some sort. An external facing surface 56 of the window faces the wearer's outergarments and is translucent or transparent to facilitate viewing of the sensor. Suitable materials for this external facing surface may be selected from the group consisting of polyethylene, polypropylene, polyester, polystyrene, polyvinyl chloride, polyurethane, polycarbonate, polyacrylate, PTFE, and combinations thereof. The window 64 of the present invention may also be removably obstructed with a cover or flap. In even another embodiment the window may serve as the overlayment layer such that the sensor and window form a single unit.

The article of the present invention may be delivered to a consumer in a variety of forms. One manner for delivery is in the form of a kit for visually detecting an infant's health status. This kit comprises: a) one or more disposable absorbent articles suitable for receiving and containing bodily exudates, said article comprising a front region, a back region and a crotch region disposed between said front and back region, each region having two opposing longitudinal edges, and wherein said article further comprises a window on any one of said regions for viewing a sensor suitable for measuring a condition selected from the group consisting of temperature, dehydration, rash, pH, analyte level, skin condition, humidity, and combinations thereof and wherein the sensor is placed adjacent to and facing said window; and b) one or more of said sensors. In another embodiment, kit may comprise a tracking sheet to record readings from the sensor.

The present invention further relates to various s of using the articles of the invention. For instance, one method is that of visually detecting an infant's health status, wherein the method comprises the steps of: a) providing a caregiver with a disposable absorbent article suitable for receiving and containing bodily exudates, said article comprising a front region, a back region and a crotch region disposed between said front and back region, each region having two opposing longitudinal edges, and wherein said article further comprises a window on any one of said regions for viewing a sensor suitable for measuring a condition selected from the group consisting of temperature, dehydration, rash, pH, skin condition, analyte level, humidity, and combinations thereof and wherein the sensor is placed adjacent to and facing said window and b) donning said article onto an infant.

EXAMPLE

An absorbent article of the present invention is prepared by providing a diaper chassis as disclosed in any one of U.S. Pat. Nos. 3,860,003, 4,636,207, 4,695,278, 4,704,115, 4,795,454, 4,900,317, 4,909,803 (Reissued as USRE34920), 5,085,654, 5,492,751, 6,476,288, 6,627,787, 5,507,760, 5,609,587, 5,635,191, 5,643,588, 6,118,041 and SIR H1630. The sensor includes a thermochromic liquid crystalline material that is commercially available from Liquid Crystal Resources, LLC as "Unsealed Cholesteric Liquid Crystal Clearing Point Formulation with Hysteresis". The resulting thermochromic liquid crystalline material is temperature insensitive formula and is coated onto the underlayment layer via a slot coater. The thermochromic liquid crystalline material exhibits the follow characteristics upon application to the underlayment layer:

1. Type—cholesteric compounds, temperature insensitive (aka "clearing point" liquid crystalline materials)
2. Preparation of thermochromic liquid crystalline material—Not encapsulated
3. Application thickness—about 50 um (2 mil)
4. Trigger temperature—about 37.8° C. or 100.0° F.
5. Accuracy—about ±0.1° C. (0.2° F.)
6. Repeatability—less than about ±0.05° C. (0.1° F.)
7. Transition span (color to clear)—about 0.3° C. (0.6° F.)
8. Hysteresis or delay (aka time that temperature is above or below trigger temperature before thermochromic liquid crystalline material transitions)—30 seconds The thermochromic liquid crystalline material is designed to reflect a green wavelength of light at temperatures below about 100° F. (i.e., appear green) and become transparent at temperatures above about 100° F. The thermochromic liquid crystalline material may be altered to reflect other parts of the visible light spectrum such as red or blue and to function at alternative temperature set points ranging from about 99.5° F. to about 102° F. Other parameters such as the delay, accuracy or precision can deviate from what is specified above and the sensor may also satisfactorily function as a skin temperature measurement device. Alternatively chiral thermochromic liquid crystal formula such as those that are commercially available from Liquid Crystal Resource, LLC can also be used.

The thermochromic liquid crystalline material may be applied to a substrate at uniform thickness in a circular pattern 1.5 cm. in diameter. The thermochromic liquid crystalline material is disposed on the underlayment layer in such a way that when the overlayment layer is placed over the thermochromic liquid crystalline material, the material covers a circular area having about a 1.5 cm diameter on an underlayment layer. An indicia, e.g. a smiling face, is printed with black ink on the overlayment layer and an additional frowning face in green ink where the green ink matches the green of the thermochromic liquid crystalline material. The initial appearance of the indicia is a black printed smiling face on the overlayment layer, which is placed over the green thermochromic liquid crystalline material. Those areas of, the graphical indicia that are unprinted with black ink appear transparent initially over the thermochromic liquid crystalline material which is green in color. As designed, this sensor will change in appearance from the smiling face graphical indicia to a frowning face when an infant's skin temperature of greater than about 100° F. is detected. This change in the graphical indicia is effected by the green color of the thermochromic liquid crystalline material changing to a transparent and uncolored appearance and revealing a printed black surface of the underlayment layer.

The overlayment layer is adhesively and/or heat sealed to the underlayment layer in such a way that the thermochromic liquid crystalline material is undisturbed. The seal must be complete to prevent the degradation of the thermochromic liquid crystalline material due to long term exposure to oxygen. In addition, the seal protects the temperature sensing material from being contaminated with impurities that can negatively impact their performance. The substrate may be sealed to the cover using adhesives, heat sealing, clamping, ultrasonic bonding, or any other suitable method. The sensor is then adhesively attached to a polyethylene window that is slightly larger than the sensor as shown in FIG. 4, with the center of the sensor located between a reasonable amount (e.g., 4-5 cm for Pampers size 2) below the front edge of the disposable diaper in the front waist region.

In another embodiment, the underlayment and overlayment layers may each be cut into 1.25"×1.25" squares. The underlayment layer, which may be clear, has a 0.5 inch diameter black circle printed under it. A 0.5" square of liquid crystal material is slot coated onto the underlayment layer. Then, a clear overlayment layer is bonded to the underlayment layer at the peripheral edges using adhesive. The part of the liquid crystal material over the black circle appears green at normal temperatures (the part that is over the clear or white appears colorless). When the temperature is elevated, the green liquid crystal becomes colorless and the black circle is observed.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm".

All documents cited in the Detailed Description of the Invention are, in relevant part, incorporated herein by reference; the citation of any document is not to be construed as an admission that it is prior art with respect to the present invention. To the extent that any meaning or definition of a term in this written document conflicts with any meaning or definition of the term in a document incorporated by reference, the meaning or definition assigned to the term in this written document shall govern.

While particular embodiments and/or individual features of the present invention have been illustrated and described, it would be obvious to those skilled in the art that various other changes and modifications can be made without departing from the spirit and scope of the invention. Further, it should be apparent that all combinations of such embodiments and features are possible and can result in preferred executions of the invention. Therefore, the appended claims are intended to cover all such changes and modifications that are within the scope of this invention.

What is claimed is:

1. A method of visually detecting an infant's health status, said method comprising the steps of:
   a. providing a disposable absorbent article adapted to be worn about a wearer's lower torso, suitable for receiving and containing bodily exudates and for visually detecting health-related conditions of the wearer, said article comprising:
      a front waist region having a lateral front end edge, a back waist region having a lateral back end edge, and a crotch region disposed between said front and back waist regions, each region having two opposing longitudinal edges;
      a window on said front waist region; and
      a sensor placed adjacent to and facing said window, the sensor comprising a thermochromic skin temperature measurement device adapted for application to the skin and adapted to undergo a change of appearance from a first appearance at a skin temperature lower than about 99.5° F. to 102° F. to a second appearance at a skin temperature higher than about 99.5° F. to 102° F., said thermochromic skin temperature measurement device having a center and being disposed in said front waist region with the center located between 4-5 cm below the front end edge,
   b. donning said article onto an infant; and
   c viewing the sensor and thereby detecting a condition of the infant comprising elevated body temperature.

2. The method of claim 1 wherein said sensor is adhesively attached to said window.

3. The method of claim 1 wherein said sensor is attached to said window via a hook and loop fastener.

4. The method of claim 1 wherein said window is transparent or translucent.

5. The method of claim 1 wherein said sensor comprises a thermochromic temperature sensor comprising a thermochromic material selected from the group consisting of thermochromic inks, liquid crystalline materials, thermochromic dyes, and combinations thereof.

* * * * *